United States Patent [19]
Barker et al.

[11] Patent Number: 5,732,836
[45] Date of Patent: *Mar. 31, 1998

[54] INDICATOR CLOSURE FOR CLOSING A CONTAINER

[75] Inventors: Allan Barker; Gage Garby, both of Boulder, Colo.

[73] Assignee: Senetics, Inc., Lionville, Pa.

[*] Notice: The term of this patent shall not extend beyond the expiration date of Pat. No. 5,009,338.

[21] Appl. No.: 153,531

[22] Filed: Nov. 16, 1993

Related U.S. Application Data

[63] Continuation of Ser. No. 21,735, Feb. 23, 1993, Pat. No. 5,261,548, which is a continuation of Ser. No. 718,354, Jun. 21, 1991, abandoned, which is a continuation-in-part of Ser. No. 641,759, Jan. 17, 1991, abandoned, which is a continuation-in-part of Ser. No. 306,485, Feb. 3, 1989, Pat. No. 5,009,338.

[51] Int. Cl.$^6$ .................. B65D 55/02; B65D 51/18
[52] U.S. Cl. .................. 215/230; 215/203; 215/216; 215/220
[58] Field of Search .................. 215/204, 211, 215/213, 219, 220, 222, 230, 203, 216; 206/459.1; 116/308

[56] References Cited

U.S. PATENT DOCUMENTS

| | | | |
|---|---|---|---|
| 4,011,829 | 3/1977 | Wachsmann et al. | 116/121 |
| 4,057,159 | 11/1977 | Fillmore et al. | 215/222 |
| 4,365,722 | 12/1982 | Kramer | 215/220 |
| 4,528,933 | 7/1985 | Allen | 116/308 |
| 4,749,093 | 6/1988 | Trick | 215/220 |
| 4,753,189 | 6/1988 | Mastman et al. | 116/308 |
| 4,782,966 | 11/1988 | Thackrey | 215/230 |
| 4,834,251 | 5/1989 | Ya | 215/222 |
| 4,913,083 | 4/1990 | Valvo et al. | 116/308 |
| 5,009,338 | 4/1991 | Barker | 215/230 |
| 5,082,129 | 1/1992 | Kramer | 215/221 |
| 5,184,739 | 2/1993 | Kusz | 215/220 |
| 5,261,548 | 11/1993 | Barker et al. | 215/230 |

*Primary Examiner*—Allan N. Shoap
*Assistant Examiner*—Nathan Newhouse
*Attorney, Agent, or Firm*—Davis, Graham & Stubbs LLP

[57] ABSTRACT

A closure for a container, including means for counting and indicating the number of times the closure has undergone a cycle of closing and opening the container, and further including means for incorporating the closure into means for resisting the opening of the container by a child. In a preferred embodiment, the closure includes an outer cover having an indicator symbol window an indicator symbol carrier rotatably mounted in the outer cover with indicator symbols visible through the indicator window, tooth and pawl means for allowing one-way rotation of the outer cover relative to the indicator symbol carrier to allow the advancement of the window and an audible click as the pawl passes over a tooth to confirm proper advancement, lost motion means for positively assuring the advancement of the window by one and only one indicator symbol upon each cycle, and a closure mechanism requiring the application of an axial force urging the closure toward the container while applying a rotational force to disengage the closure from the container.

5 Claims, 8 Drawing Sheets

INDICATOR CLOSURE FOR CLOSING A CONTAINER

This application is a continuation of application Ser. No. 08/021,735 filed Feb. 23, 1993, now U.S. Pat. No. 5,261,548 issued Nov. 16, 1993, which is a continuation of application Ser. No. 07/718,354, filed on Jun. 21, 1991, now abandoned, which is a continuation-in-part of application Ser. No. 07/641,759, filed Jan. 17, 1991, now abandoned, which is a continuation-in-part of application Ser. No. 07/306,485 filed Feb. 3, 1989, now U.S. Pat. No. 5,009,338 issued Apr. 23, 1992.

BACKGROUND OF THE INVENTION

The present invention relates to closure members for containers, bottles and the like and, more particularly, to closure members having indicator means to indicate the number of times the container has been opened. The invention can also be used for any other application in which the number of times a given activity is performed must be indicated.

In the medical field, medical drugs have a predetermined therapeutic range in which the effects of taking the drug are beneficial. Under-utilization of a drug may endanger the user with the drug's side effects without reaching levels necessary for a therapeutic action. On the other hand, overutilization may cause side effects or toxicity to a much greater extent than any possible benefit. Thus it is critically important that a patient follow prescribed directions on medications, yet frequently patients forget whether they have taken medication and either omit doses or repeat them.

A considerable number of pill-timing schemes have been used to solve the problem of reminding a patient to take a dose of medicine or reminding him he has already taken the dose. The most used ones involve some scheme of compartmentalization of the necessary medication, such that the pills are placed in compartments that are labeled by day, dose number or time of day, or that are serially numbered. These devices are reasonably satisfactory if a responsible person is available and has the time and patience to fill the compartments properly.

In dispensing pills of a single type, a number of window-containing bottle caps have been invented. Through the window a movable element marked with an index is visible. In only a few devices does the indicating element index in position relative to the window each time the cap is loosened, removed, replaced, and re-tightened. Thus, by looking at the index mark displayed through the window, a user can see where in repetitive sequence of dose he or she is.

One of the most serious disadvantages of prior art devices of the window indexing type is that there is no warning to the user in case the user does not turn the device far enough during the opening or closing to properly advance the window. Unless the user is alert to the index value before opening and then after closing such devices, the user will be unaware that the window failed to advance to a new index. Most users, especially the elderly who may not understand how the device operates, will not be this alert to the functioning of the device. In addition, most prior art devices fail to provide positive locking in both directions of movement; thus, the index may be moved appropriately when the device is opened or closed, but additional movement is not prevented when the device is moved in the opposite direction. This allows the index to drift, often causing failure or an incorrect reading, particularly after the device has been used over a period of time.

The device of U.S. Pat. No. 4,011,829 issued Mar. 15, 1977 to Wachsmann, et al., attempts to provide positive locking in both directions, but because of the direction of the tooth designed to prevent movement of the index upon closure, the device may not work reliably, particularly after wearing with use. Also, the device of Wachsmann does not provide space for the ratchet teeth to slide past the engagement teeth when the device is moving in a direction wherein such teeth should disengage, which may cause unreliable operation over a period of time. Another drawback of this device is its inclusion of a complicated "child proofing" feature with the indexing feature, which makes the device quite complex. Other features of this device, such as the method of providing the lost motion drive and the requirement of a post in the middle of the elements to hold the device together, also increase its complexity.

The device of U.S. Pat. No. 3,151,599 issued Oct. 6, 1964 to Livingston provides positive locking in both directions, but it does so by means of very closely spaced projections that would be difficult to manufacture economically. Furthermore, this device does not provide space for the projections to move while sliding past each other when not engaged.

The device of U.S. Pat. No. 4,666,051 issued May 19, 1987 to Trick has an indicator wheel with a serrated rim projecting above and below the plane of the wheel. The serrations engage mating serrations in upper and lower elements in order to drive the indicator mechanism. The serrations are rigid and, therefore, tend to wear excessively as they slide past one another.

The device of European Patent Application No. 87100917.2, published Jul. 27, 1987, by Schwab, has a cup-shaped exterior element that engages a frustoconical closure cap. The Schwab device is somewhat complicated in design and manufacture. The device of U.S. Pat. No. 4,220,247 issued Sep. 2, 1980 to Kramer also includes a cup-shaped exterior element which engages an inner element.

Other devices in the art include U.S. Pat. No. 4,511,050 by Nicol; U.S. Pat. No. 4,365,722 by Kramer; U.S. Pat. No. 4,749,093 by Trick; U.S. Pat. No. 4,782,966 by Thackrey; U.S. Pat. No. 4,753,189 by Mastman; U.S. Pat. No. 4,705,182 by Newel-Lewis; U.S. Pat. No. 4,662,520 by Griffen; U.S. Pat. No. 4,641,759 by Kelley; U.S. Pat. No. 4,634,012 by Kelley; U.S. Pat. No. 4,562,933 by Dennis; U.S. Pat. No. 4,528,933 by Allen; U.S. Pat. No. 4,511,050 by Nicol; U.S. Pat. No. 4,548,157 by Hevoyan; U.S. Pat. No. 4,501,370 by Kelley; U.S. Pat. No. 4,489,834 by Thackrey; U.S. Pat. No. 4,432,300 by Lyss; U.S. Pat. No. 4,419,016 by Zoltan; U.S. Pat. No. 4,405,045 by Villa-Real; U.S. Pat. No. 4,357,192 by Moser; U.S. Pat. No. 4,347,804 by Villa-Real; U.S. Pat. No. 4,094,408 by Ford; U.S. Pat. No. 3,996,879 by Walton; U.S. Pat. No. 3,960,713 by Carey; U.S. Pat. No. 3,926,326 by Grau; U.S. Pat. No. 3,921,568 by Fish; U.S. Pat. No. 3,887,099 by Gillman; U.S. Pat. No. 3,753,417 by Garby; U.S. Pat. No. 3,446,179 by Bender; U.S. Pat. No. 3,334,731 by Dale; U.S. Pat. No. 2,943,730 by Tregilgas; U.S. Pat. No. 2,939,597 by Greene; U.S. Pat. No. 2,587,147 by Guion; and U.S. Pat. No. 498,851 by Adsit.

It is thus apparent from a review of this art that there is a need for an improved indicator cap in the manner of the present invention that provides positive controlled movement of the index on both opening and closing of the device, while also providing an indication to the user that the index has functioned properly each time the device is used. Preferably, the basic design of such a device can also be used in other applications where it is necessary to have a record of the number of times a given event occurs.

It is also apparent from a review of this art that there is a need for an improved indicator cap that can be used as a child-resistant closure. Preferably, such a cap would have a minimum of parts, would be easily manufactured and assembled using standard injection molding and assembly methods, and could be used with ordinary containers that are not necessarily specially designed for the cap.

SUMMARY OF THE INVENTION

It is an object of the present invention to provide an indicator device to indicate the number of times a given event has occurred. Such an invention may have applicability in the control of chemical containers, the development of photographic film and many other areas.

More particularly, it is an object of the present invention to provide an indicator cap for a medication dispensing bottle or the like that provides an indication each time the bottle is opened and then reclosed.

It is another object of this invention to provide a device that has positive control of the index member during both the opening and the closing motions and to require the advancement of the index member by one and only one new index during each complete opening and closing cycle.

Yet another object of the invention is to provide an audible sound to confirm that the device has been rotated sufficiently to move the index to the next location and to also provide an audible sound when the device has been rotated sufficiently to re-cock the device for the next open-close sequence.

Still another object is to provide space within the device for the locking mechanisms to slide past each other when not engaged to allow such mechanisms to work reliably over a long period of time.

Another object of the present invention is to combine functions usually requiring several components into single components to reduce the complexity of the device and provide ease of manufacturability and assembly using standard injection molding and assembly techniques.

Another object of the present invention is to provide an indicator assembly that can easily be fitted to an ordinary container without requiring any special modifications to the container itself.

Another object is to provide a device with indicator symbols that can be sensed by touch such as raised letters or braille.

Another object is to provide a device that can be easily grasped by elderly or impaired patients, as by including grasp-facilitating elements on the device.

Another object is to provide a device which is easily manufactured and assembled with a minimum of parts.

A device achieving some of these objects is disclosed in U.S. patent application Ser. No. 07/641,759 filed Jan. 17, 1991 (of which the present application is a continuation-in-part) and U.S. Ser. No. 07/306,485 filed Feb. 3, 1989 (of which the U.S. Ser. No. 07/641,759 application is a continuation-in-part), the contents of both of which are hereby incorporated by reference.

DESCRIPTION OF THE PREFERRED EMBODIMENTS

Figure 1:
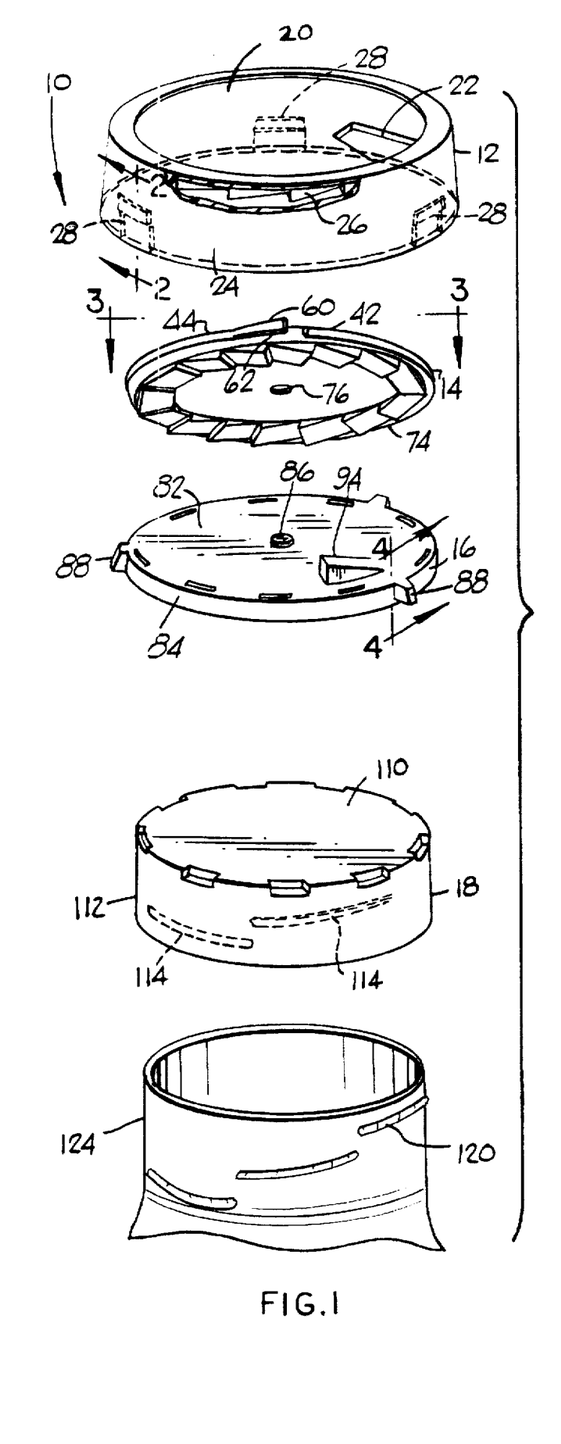
FIG. 1 is an exploded perspective view showing an embodiment of the present invention along with the neck of a container to which the invention can be attached.

Four-Piece Threaded Version. A preferred embodiment of the invention 10 is shown in FIG. 1. This preferred embodiment includes an outer cover 12, an indicator wheel 14, a ratchet wheel 16 and an inner cover 18. The outer cover includes a top circular portion 20 with a window 22 and a depending skirt 24. The lower surface of the top circular portion 20 has a set of teeth 26.

Figure 2:
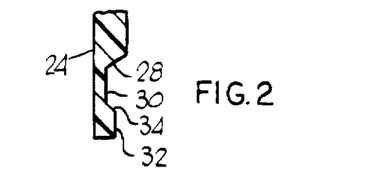
FIG. 2 shows a detail of the annular grooves in the outer cover, taken along line 2—2 of FIG. 1.

The inner surface of the depending skirt 24 has a set of grooves 28 (three in the embodiment shown), as better seen in FIG. 2. The grooves 28 are in the annular direction around a portion of the depending skirt inner surface, and include a deep groove portion 30 and a shallow groove portion 32 connected by a ramp 34 which may be perpendicular to the two groove portions or may be sloped relative to the two groove portions. The function of the grooves is to receive the ratchet wheel tabs as described in some detail below.

The window 22 in the circular top portion 20 of the outer cover 12 may be trapezoidal in shape as shown in FIG. 1 or, alternatively, may be circular in shape or may be circular on its upper edge and sloped to trapezoidal on its lower edge. In the later alternative especially, the window can be used with an indicator wheel having raised or recessed alphanumeric symbols or braille symbols so that the user can sense the symbols with his finger even though his vision may be physiologically or environmentally impaired.

Figure 3:
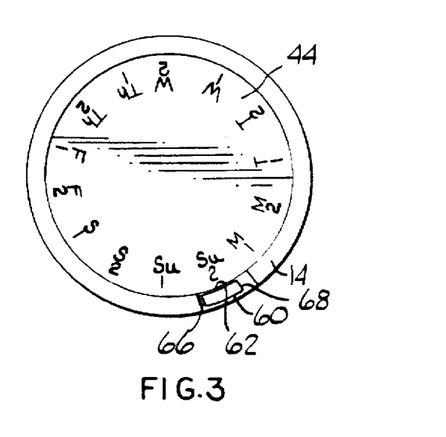
FIG. 3 shows a detail of the top of the indicator wheel, taken along line 3—3 of FIG. 1.

The indicator wheel 14 includes a circular top portion 42 containing a set of indicator symbols 44 to indicate a day of the week and a dose number of that day. For example, the symbols may be Su1, Su2, M1, M2, etc. as shown in FIG. 3 to indicate a dosage schedule of two per day. Alternatively, of course, the indicator symbols may be 1, 2, 3, 1, 2, 3, etc. to indicate a dosage schedule of three per day, or Su, M, Tu, etc. to indicate a dosage schedule of one per day, and so on.

The total number of indicator symbols 44 on the indicator wheel 14 should be evenly divisible into the total number of teeth 26 in the outer cover 12. Otherwise, the indicator symbols will not advance one at a time past the outer cover window 22 as the device is operated unless the indicator wheel has some blanks in place of indicator symbols. Preferably, the number of indicator symbols 44 together with the number of any blanks that may be necessary is exactly equal to the number of outer cover teeth 26.

In the region of the outer perimeter of the indicator wheel 14 is a ratchet 60 which is spaced apart from the body of the indicator wheel by a space 62 underneath it, an annular slot on the radially inner side of it, and a leading edge slot 66 adjacent the leading edge of it. The ratchet is flexibly connected to the indicator wheel of only the trailing edge 68. This flexible connection along with the slots and space 62 allow the ratchet to flex as it passes over the outer cover teeth 26 of the outer cover 12.

The bottom surface of the indicator wheel 14 includes a set of indicator wheel teeth 74. The number of indicator wheel teeth involves the same considerations as the number of outer cover teeth, as discussed above, and preferably is exactly equal to the total of the number of indicator symbols and the number of blanks on the upper circular portion of the indicator wheel. The bottom surface of the indicator wheel 14 also preferably has an axially extending center hole 76 to receive the hub of the ratchet wheel in the manner described below.

Figure 4:
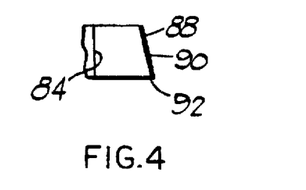
FIG. 4 shows a detail of the ratchet wheel tabs, taken along line 4—4 of FIG. 1.

The ratchet wheel 16 includes a circular upper portion 82 and a depending skirt 84. The center of the circular upper portion 82 has an axially extending center hub 86 which mates with the center hole 76 of the indicator wheel. Around the outer circumference of the circular upper portion 82 is a set of tabs 88 extending radially outward. As better seen in FIG. 4, the tabs 88 have a sloping ramp 90 and a locking edge 92 at the lower end of the sloping ramp 90. The tabs 88 engage the grooves 28 in the inner surface of the depending skirt 24 of the outer cover 12 and, therefore, are numbered and configured to align therewith so that the ratchet wheel can be attached to the outer cover by the tabs and grooves while still allowing a predetermined amount of rotation of one relative to the other by sliding the tabs annularly through the grooves.

The ratchet wheel also includes a ratchet wheel pawl 94 flexibly attached to the circular upper portion 82. The pawl 94 rests in and is attached to one end of a rectangular cutout in the circular upper portion to allow it to flex up and down as it rides over the indicator wheel teeth 74 on the bottom of the indicator wheel 14.

Another element of the ratchet wheel 16 is a set of lugs 102 extending downward from the lower surface and radially inward from the depending skirt 84. The lugs 102 occupy a space at the joining of the circular upper portion 82 (on its lower side) and the depending skirt 84 (on its inner side) and are numbered and configured to mate with the notches on the upper surface of the sealing cover as described below.

Figure 5:
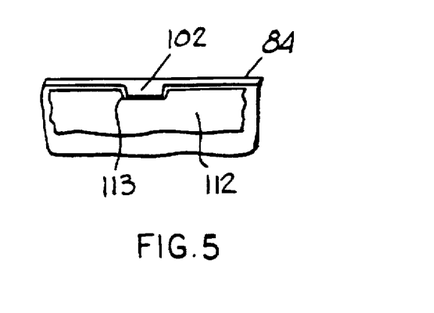
FIG. 5 shows a detail of the lugs and notches of the ratchet wheel and sealing cover of FIG. 1.

The sealing cover 18 includes a circular upper portion 110 and a depending skirt 112. The circular upper portion 110 has a set of notches 113 numbered and configured to mate with the lugs 102 on the ratchet wheel 16 and are better shown in FIG. 5. The purpose of the lugs and notches are to engage the ratchet wheel with the sealing cover upon the application of an axial force pushing the two together when the device is turned in the direction to unscrew it from the container. The lugs and notches are configured such that no axial force (other than that provided by gravity) is required to engage them when the device is turned in the direction to screw it onto the container. It can be appreciated that the exact number and configuration of the lugs and notches is not critical so long as they effectively engage one another upon the application of an axial force within the easy capability of an adult, and they disengage upon the release of such force. Lug and notch arrangements such as this are well-known in the field of child-resistant closures, and need not be described in any more detail here. The inner surface of the depending skirt 112 of the sealing cover 18 has threads 114 to mate with threads 120 on the outer surface of the neck of the container 124.

Although the embodiment shown has teeth on the lower surface of the indicator wheel and a mating pawl on the upper surface of the ratchet wheel, the arrangement could also be reversed so that the pawl is on the lower surface of the indicator wheel and the teeth are on the upper surface of the ratchet wheel. Similarly, the teeth on the outer cover and the pawl on the indicator wheel could be reversed so that the pawl is on the outer cover and the teeth are on the indicator wheel, and the grooves on the outer cover and tabs on the ratchet wheel could be reversed so that the grooves are on the ratchet wheel and the tabs are on the outer cover. Finally, the direction of the teeth and pawls may be reversed, so that the indicator wheel advances when the device is closed rather than when it is opened. The possibility of reversing the elements in these ways applies to all of the embodiments described herein. Whether the elements should be reversed or not may depend on molding and assembly considerations. Also, the mating pawls may include a plurality of pawls or even an entire set of pawls such as a circumferential row of teeth. Alternatively, the teeth with which the pawls mate may be replaced by holes or other depressions or other means for engagement.

In operation, the preferred embodiment 10 of FIGS. 1–5 can be attached to the container 124 by placing it onto the top of the container and turning it in a clockwise direction (or counterclockwise direction if the threads were left-handed). The turning of the outer cover 12 is translated into a turning of the indicator wheel 14 by the outer cover teeth 26 engaging the indicator wheel pawl 60.

The turning of the indicator wheel 14 is translated into a turning of the ratchet wheel 16 by the outer cover grooves 28 engaging the ratchet wheel tabs 88. First, however, the outer cover 12 must be turned sufficiently so that the wall of the outer cover grooves 28 contacts the ratchet wheel tabs 88. Until the outer cover is turned that necessary amount, the tabs slide through the grooves, and the rotating indicator wheel slides over the stationary ratchet wheel. The sliding of the indicator wheel over the ratchet wheel causes the ratchet wheel pawl 94 to slide over the indicator wheel teeth 74, causing an audible click when the pawl snaps over a tooth to confirm the proper operation of the device.

Once the outer cover is turned sufficiently so that the ratchet wheel tabs are against the end wall of the outer cover grooves, the ratchet wheel begins to turn. The turning of the ratchet wheel is translated into a turning of the sealing cover 18 by the ratchet wheel lugs 102 engaging the sealing cover notches 113. As the sealing cover 18 turns relative to the container 124, the sealing cover threads engage the container threads to close and seal the container.

To remove the device 10 from the container, it is turned in the opposite direction relative to the container while an axial force is applied urging the outer cover 12 toward the container 124 in order to engage the ratchet wheel lugs 102 with the sealing cover notches 113. The initial turning of the outer cover 12 will not be translated into a turning of the sealing cover 18, however. Instead, the indicator wheel 14 will remain stationary as an outer cover tooth 26 slides over the indicator wheel pawl 60. This sliding will advance the outer cover window 22 to a new indicator symbol, thereby recording that the device has been opened. As the window advances one full indicator symbol, the indicator wheel pawl 60 will pass over one complete outer cover tooth 26 and, when it does, the pawl will snap over the edge of the tooth. This results in an audible click confirming the proper window advancement.

Also stationary during the initial turning of the outer cover 12 is the ratchet wheel 16. This is because the ratchet wheel tabs 88 slide through the outer cover grooves 28. At the same time, the ratchet wheel pawl 94 engages the indicator wheel teeth 74 to prevent any movement between the indicator wheel and ratchet wheel.

When the ratchet wheel tabs 88 finally have slid through the outer cover grooves 28 so that the tabs are against an end wall of the grooves, the groove end wall applies a force against the tabs so that the ratchet wheel 16 begins to turn with the outer cover 12. This turning of the ratchet wheel 16 translates into a turning of the sealing cover 18, provided that the necessary axial force is applied to maintain the engagement between the ratchet wheel lugs 102 and sealing cover notches 113. The sealing cover threads 114 then unscrew from the container threads 120 to allow the device 10 to be removed from the container. The device is at that time in a proper configuration to be put back onto the container, with the indicator wheel tabs 88 at one end of the outer cover grooves 28.

Figure 6:
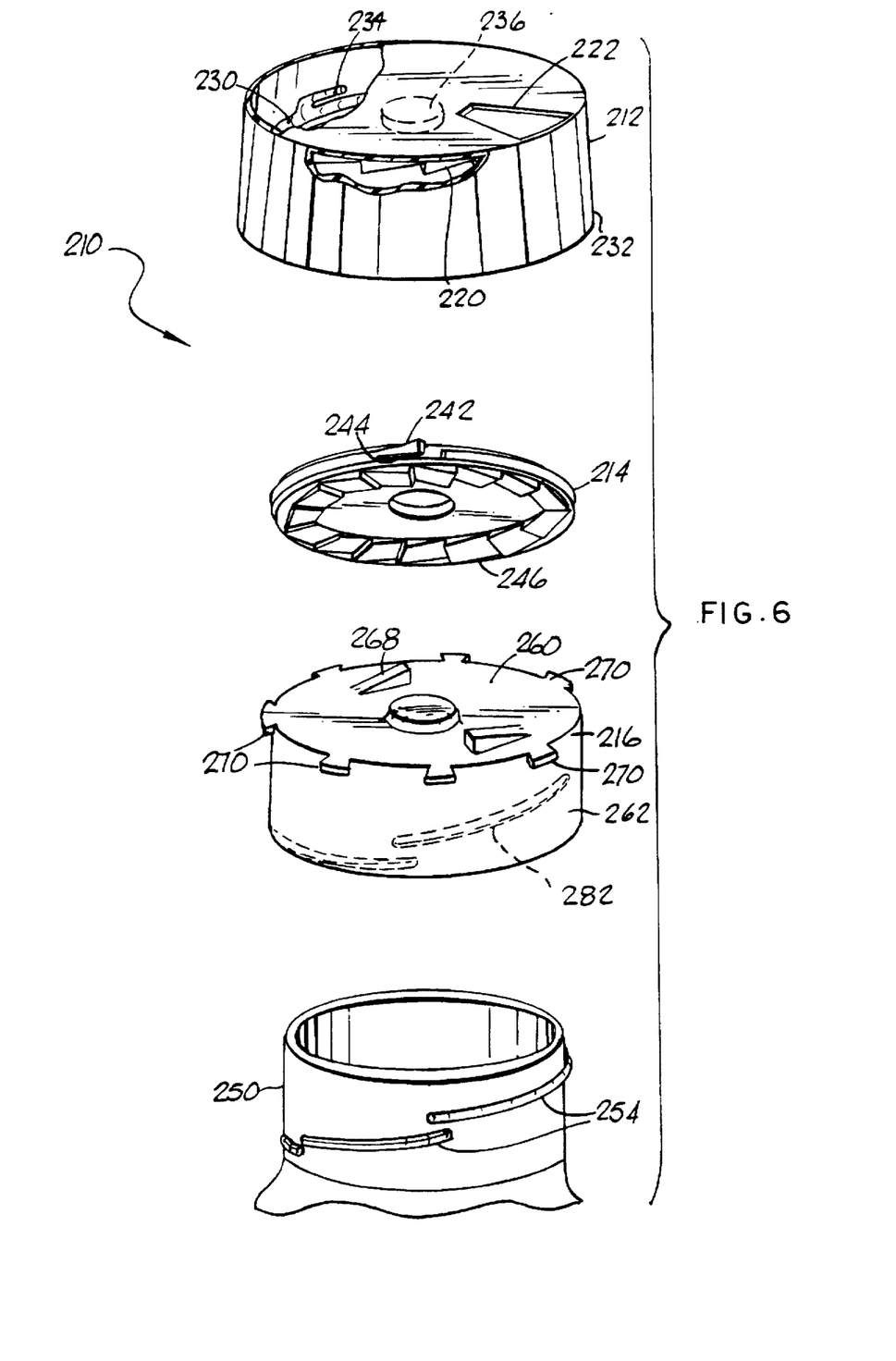
FIG. 6 is an exploded perspective view showing another embodiment of the present invention.

Three-Piece Threaded Version. Another preferred embodiment of the invention 210 is shown in FIG. 6. That embodiment includes an outer cover 212, an indicator wheel 214 and a ratchet cover 216. The outer cover 212 has a set of outer cover teeth 220 and an indicator symbol window 222 in the manner of the four-piece threaded version described above, and will not be further described here. The outer cover 212 also includes an annular raceway 230 extending around the radially inner surface of a depending skirt 232. A set of teeth 231 to permit only one-way travel, as explained below, are on the raceway surface. Alternatively, the device may include other means to limit the travel to one direction, such as a set of teeth and pawl on the outer surface of the ratchet cover skirt and inner surface of the outer cover skirt. The raceway 230 has a set of engaging grooves 234 extending upward from the raceway and in one circumferential direction. The raceway 230 and grooves 234 receive a set of tabs on the ratchet cover 216 as described in more detail below. The inner surface of the top of the outer cover may include an axially extending hub 236 that mates with a hole in the indicator wheel in the manner described below.

The indicator wheel 214 has a central hole 240 which mates with the axially extending hub 236 on the inner surface of the top of the outer cover 212 to help maintain the indicator wheel and outer cover coaxial. The top of the indicator wheel 214 has a ratchet pawl 242 which engages the outer cover teeth 220. The bottom surface of the pawl has a recessed flat 244 to allow the pawl some space to flex as it passes over the teeth. The pawl is spaced apart from the body of the indicator wheel in the radial direction by a slot and is flexibly attached to the indicator wheel at its base in the same manner as the indicator wheel 14 of the four-piece threaded version described above. The bottom surface of the indicator wheel has a set of indicator wheel teeth 246 around the periphery which engage pawls on the ratchet cover in the manner described below.

The ratchet cover 216 has a circular upper portion 260 and a depending skirt portion 262. The top surface of the circular upper portion 260 has a spring means 264 to apply an axial force urging the indicator cover 214 and outer cover 212 apart from the ratchet cover 216 so that an axial compressive force is necessary to overcome such force to engage the tabs of the ratchet cover in the engaging grooves of the outer cover in the manner described below. In the preferred embodiment, the spring 264 is a diaphragm that is thinned and raised relative to the indicator wheel itself. The diaphragm is made from the same resilient plastic material as the rest of the indicator wheel, and serves to bias the outer cover 212 away from the indicator wheel 214 and container 250. This biasing away of the outer cover must be overcome by application of an axial force in order to engage the ratchet cover lugs 270 with the outer cover engaging grooves 234, thereby achieving a resistance to opening by a child, in the manner described below. Alternatively, the outer cover may be biased away from the container by constructing the ratchet cover pawls 268 so that they extend upwardly to a point where they must be flexed downward in order to assemble the device. Other methods for biasing the outer cover away from the container will be apparent to those skilled in the art, such as leaf springs or resilient compressible liners, and each of these may be used on each embodiment described herein that uses biasing means.

The upper portion 260 of the ratchet cover 216 also has at least one (two in the embodiment shown) pawl 268 protruding upwardly to engage the indicator wheel teeth 246. The pawl covers a cutout in the upper portion and is slightly smaller than the cutout so that the pawl can flex at its base where it attaches to the upper portion into the cutout as it passes over the indicator wheel teeth 246. As in the case of the other embodiments, the teeth 246 and pawl 268 may be reversed, so that the pawl is on the indicator wheel and the teeth are on the ratchet wheel.

Figure 6A:
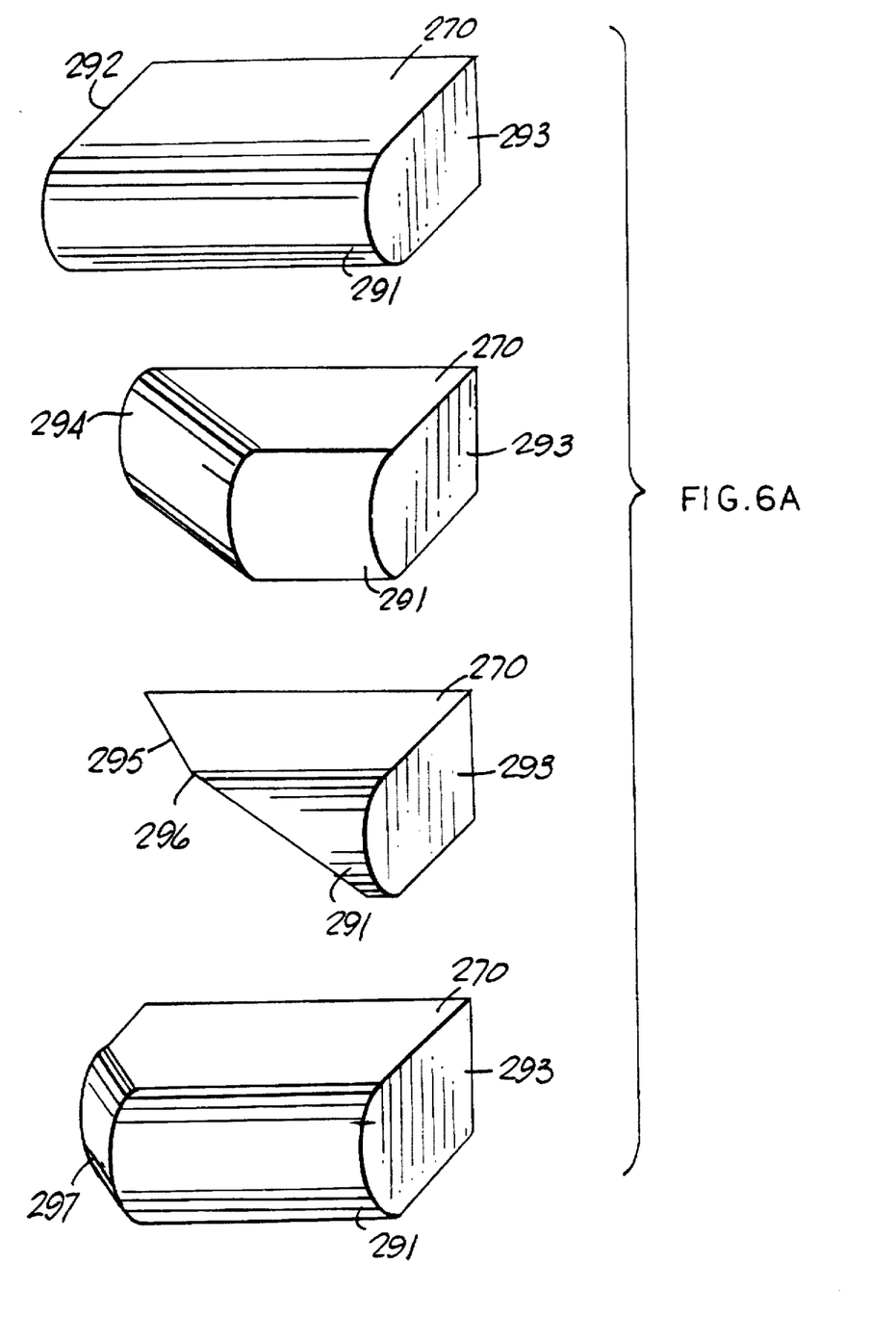

On the radially outer surface of the depending skirt 262 of the ratchet cover 216, at the upper edge thereof where it meets the top surface of the upper portion 260, are a set of radially extending tabs 270. The tabs 270 are configured with a radially outer surface. Various configurations are possible for the tabs, as shown in FIG. 6A. In each of the configurations of FIG. 6A, the radially outer edge 291 is rounded to nest into the rounded radially outer surface of the annular raceway 230 and engaging grooves 234. In all the embodiments, the trailing edge 293 is planar and substantially parallel to the radially outer edge 291, so that the trailing outer edge 294 engages the one-way teeth 231 in the raceway 230. In the top embodiment shown in FIG. 6A, the tabs are generally rectangular with the exception of the rounded radially outer edge 291, and the leading edge 292 is substantially parallel to the trailing edge 293 that are planar and approximately perpendicular to the radially outer edge 291. In the second embodiment shown in FIG. 6A, the tabs have a beveled and rounded leading edge 294 and a planar trailing edge 293. The beveled leading edge 294 assists in the tab 270 sliding into the engaging grooves 234. In the third embodiment shown in FIG. 6A, the leading edge 295 is a beveled plane that cuts the tab 270 so that the top of the leading edge slopes rearwardly as one travels radially outward, and the radially outer edge of the leading edge slopes downwardly as one travels toward the trailing edge. This results in an angular point 296 where the top of the leading edge meets the radially outer edge of the leading edge, which catches the engaging grooves 234 as the tabs 270 are engaged therein. In the last embodiment shown in FIG. 6A, the leading edge 297 is rounded and partially bevelled to assist in the tab 270 engaging the engaging grooves 234 while still preserving some strength in the tab.

The tabs 270 attach the ratchet cover 216 to the outer cover 212 by being pressed into the annular raceway 230 of the outer cover 212, and they ride in that annular raceway and in the adjacent notches 234. The radially inner surface of the depending skirt 262 has a set of threads 282. The threads 282 engage mating threads 254 on the neck of a container 250.

The number of tabs 270 is preferably seven. That is because the number of index symbols on the indicator wheel (and, therefore, the number of teeth on the outer cover and indicator wheel) is usually seven (for one dose on each of the seven days of the week) or an integral multiple of seven (for more than one dose on each of the seven days of the week). If the number of tabs and engaging grooves is not seven or an integral multiple of seven, then the angular position of the tabs and engaging grooves relative to the indicator symbols will vary depending on which engaging grooves engage which tabs. While one position will result in correct alignment, the other positions may result in a misalignment where the indicator window misaligns with the indicator symbols. Other number of tabs and engaging grooves may be preferred for dosage schedules that are not multiples of seven. For example, a twelve indicator symbol indicator wheel (as in three doses a day for four days, four doses a day for three days or two doses a day for six days) would use three or four sets of tabs and engaging grooves. The key is that the number of indicator symbols be an integral multiple of the number of pairs of tabs and slots.

In operation, the preferred embodiment of FIG. 6 can be attached to the container 250 by placing it onto the top of the container and turning it in a clockwise direction (or counterclockwise if the threads are left-handed). The ratchet cover tabs 270 are normally at the terminal end of the outer cover engaging grooves 234 when the device is off the container, so the initial rotation of the outer cover causes the tabs to move through the engaging grooves and into the annular raceway while the ratchet cover remains stationary. As this relative rotation occurs between the ratchet cover and the outer cover, the outer cover is causing the indicator wheel to move with it by the engagement of the outer cover teeth 220 with the indicator wheel pawl 242. As the indicator wheel rotating with the outer cover moves relative to the ratchet cover, the ratchet cover pawl 268 passes over the indicator wheel teeth 246. As the pawl 268 snaps over a single tooth 246, it makes an audible click to confirm the proper operation of the device. The circumferential length of the outer cover engaging grooves 234 are such that the ratchet cover pawl 268 passes over one and only one tooth before the tabs 270 reach the end of the engaging grooves 234. The engagement of the tabs 270 with the teeth 231 of the annular raceway 230 will then cause the ratchet cover 216 to rotate with the outer cover 212. The rotation of the ratchet cover 216 will cause the ratchet cover threads 282 to thread onto the container threads 254, thereby closing and sealing the container 250.

To remove the device 210 from the container, it is necessary to rotate the outer cover in the opposite direction while applying an axial force to overcome the force exerted by the ratchet wheel spring 264 to cause the tabs 270 to again engage the engaging grooves 234. When the tabs engage the engaging grooves, they pass circumferentially to the terminal end. As the tabs are moving circumferentially to the terminal end of engaging grooves, the outer cover 212 is rotating while the ratchet cover 216 is stationary on the container 250. The stationary ratchet cover 216 holds the indicator wheel 214 stationary as well, by the engagement of the ratchet cover pawl 268 with the indicator wheel teeth 246. This results in an angular displacement of the outer cover indicator window 222 relative to the indicator wheel 214, thereby advancing the indicator window to the next indicator symbol. The circumferential length of the engaging grooves is such that the indicator window advances only one symbol before the tabs 270 reach the terminal end of the engaging grooves. Also while the outer cover 212 is rotating relative to the stationary indicator wheel 214, the indicator wheel pawl 242 passes over the outer cover teeth 220. As the pawl snaps over the ledge of a tooth, it makes an audible click to confirm the proper advancement of the indicator window 222 to the next indicator symbol. The tabs 270 are now at the terminal end of the engaging grooves 234 and ready for the next cycle of replacing and again removing the device on the container.

It should be noted that when the ratchet cover tabs 270 are positioned in the outer cover annular raceway 230 the outer cover can rotate only in the counterclockwise direction relative to the ratchet cover. Any attempt to rotate the outer cover in the clockwise direction will cause the ratchet cover tabs axial edges to engage the outer cover annular raceway teeth 231, thereby causing the ratchet cover to rotate clockwise with the outer cover. This arrangement ensures that any attempt to thread the device onto the container will be successful. Otherwise, the user could inadvertently leave the container open while thinking it had been closed.

Figure 7:
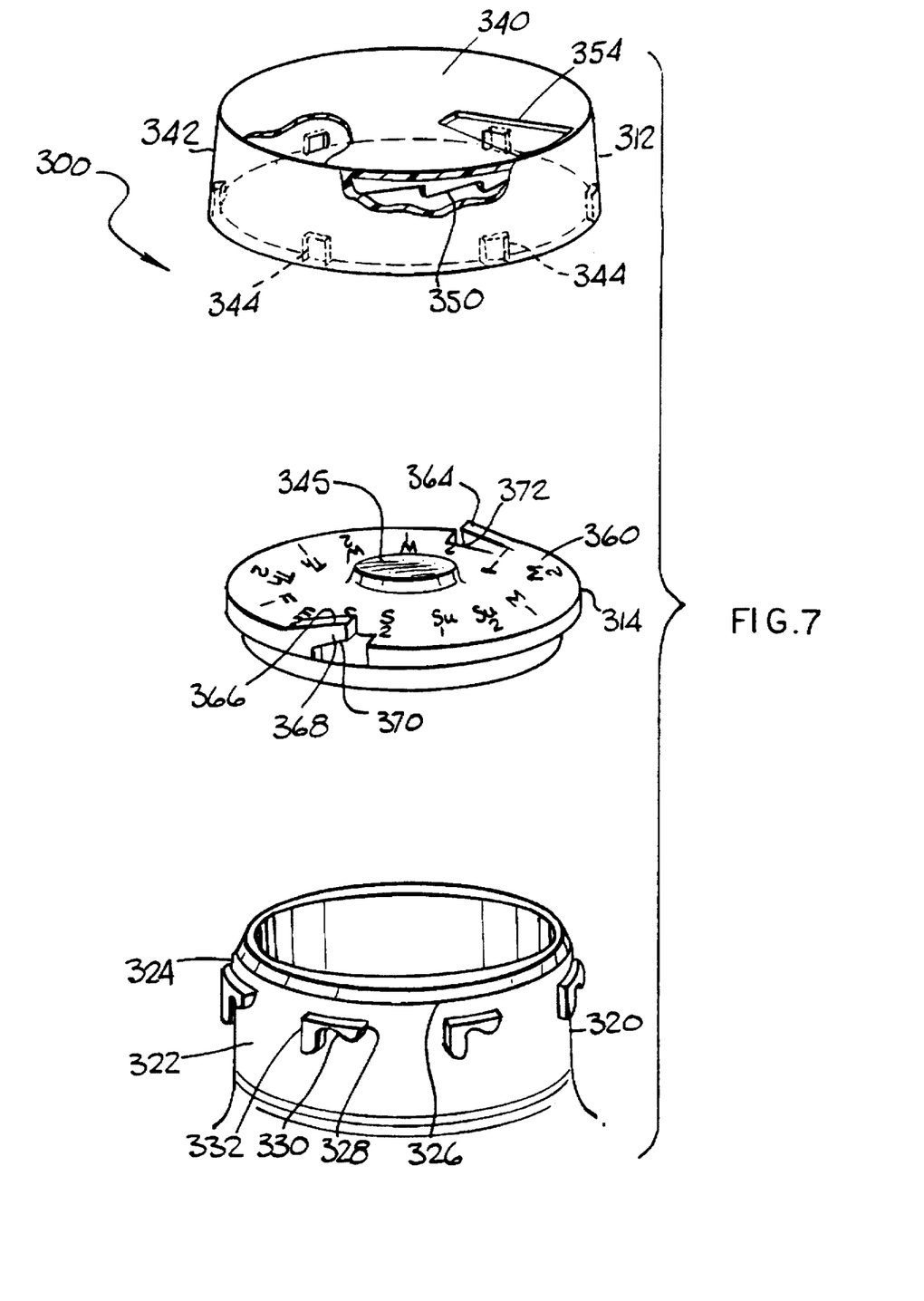
FIG. 7 is an exploded perspective view showing another embodiment of the present invention along with the neck of a container to which the invention can be attached.

Two-Piece Lug and Bayonet Version. Another preferred embodiment of the invention is shown in FIG. 7. The invention 300 includes two principal elements: an outer cover 312 and an indicator wheel 314.

The container 320 with which the present embodiment is used may be an ordinary container used with a "push-and-turn" type child-resistant closure comprising a bayonet and lug system. Such container and closure systems are well known. Briefly, they typically include a container body 322 having an upper rim 324. Around the exterior surface of the upper portion of the body 322 are a set of bayonet lugs 326, which have a leading edge 328, a notch 330 and a stop 332. The ordinary cap that is used with a container of this type is not shown, but it typically would include a resilient inner surface which springingly seals against the container upper rim 324 and a set of lugs to engage the set of bayonet lugs 326.

In operation, the ordinary cap is turned in one direction (typically clockwise as viewed from the top) so that the cap lugs ride the leading edge 328 of the bayonet lugs 326, thereby drawing the cap downward and compressing the cap resilient inner surface against the container upper rim 324. The cap lugs snap over the bayonet lug leading edges 328 to rest in the bayonet lug notches 330. The stop 332 prevents the cap lugs from advancing any farther. The dimensions of the arrangement are such that the cap has now been drawn sufficiently far downward onto the container, that the cap resilient inner surface is compressed against the container upper rim 324 to seal the container.

To remove the ordinary cap from the container 320, it is necessary to first press the cap toward the container, since otherwise any attempt to rotate the cap in one direction will be resisted by the stop 332 and in the other direction will be resisted by the rear end of the leading edge 328. The lugs of the cap can clear the rear end of the leading edge 328 only if the cap is pressed toward the container 320, so that the resilient inner surface of the cap compresses against the container upper rim 324, thereby allowing the cap lugs to drop under the bayonet leading edges 328.

Of course, there is a large number of embodiments of the push-and-turn type child resistant cap, including embodiments with a cap resilient inner surface that is integrated with the cap itself, embodiments where the bayonet lugs 326 of the container include a trailing edge to engage the container lugs so that the container can be child-resistant if the cap is turned one way but not child-resistant if the cap is turned the other way, and other embodiments. Any of these other embodiments could be used with the present invention, so long as they include at a minimum a set of bayonet lugs spaced around the container periphery.

The outer cover 312 of the present invention includes a circular top portion 340 and a depending skirt 342 attached thereto and extending axially downward. The skirt 342 has a set of integrally-formed lugs 344 spaced around the circumference of its inner surface. Each lug 344 extends radially inward from the inner surface of the skirt 342. The dimensions of the lugs 344, including the extent to which they extend radially inward and their width and thickness, is dictated by the dimensions of the bayonet lugs 326 of the container 320. The lugs 344 should enable the skirt 342 to fit over the container upper rim 324, and should ride on the bayonet leading edges 328 and nest into the bayonet notches 330 when the outer cover 312 is engaged onto and turned (clockwise in the embodiment shown) with the respect to the container 320.

The number of outer cover lugs 344 may be the same as the number of container bayonet lugs 326, but also may be different. It is only necessary that enough outer cover lugs and container bayonet lugs are engaged to effectively close and seal the container. In most applications, this will be three pairs (each pair being one bayonet and one lug), but applications might exist where two pairs or even one pair is sufficient. On the other hand, if there is a very few number of outer cover lugs and container bayonet lugs, the user will find the device inconvenient because the outer cover must then be rotated through a relatively large angle before the outer cover lugs engage the container bayonet lugs. For this reason, it is desirable to include a relatively large number (such as at least five) of either outer cover lugs or container bayonet lugs. This will ensure that the outer cover lugs will always engage the container bayonet lugs upon a small angular rotation of the outer cover relative to the container. It is important to note that it is not necessary for both the outer cover lugs and the container bayonet lugs to be of this high number. One can be of the minimum number necessary for an effective closure while the other is of the higher number. The excess of one over the other will simply result in one or more unused container bayonet lugs or outer cover lugs each time the device is closed onto the container.

The outer cover 312 includes a set of integrally-formed teeth 350 on the radially outer perimeter of the circular top portion 340 inner surface. As in the threaded embodiments described above, the number of teeth is chosen depending on the dosage schedule desired as depicted by the indicator wheel 314. For example, an indicator wheel depicting seven separate doses (such an one dose a day for seven days) will require an outer cover with seven teeth, an indicator wheel depicting fourteen separate doses (such as two doses a day for seven days or one dose a day for fourteen days) will require an outer cover with fourteen teeth, and so on. The teeth are generally wedge-shaped elements configured with a ramp and a ledge. All the teeth point in the same direction, either clockwise or counter-clockwise around the outer cap 312. In the circular top portion 340 of the outer cap 312 is an indicator window 354 extending through the top portion, which is similar to the indicator window described in connection with the threaded embodiments.

The indicator wheel 314 is a roughly disk-shaped element that nests into the outer cover 312 surrounded by the depending skirt 342. The indicator wheel may have a set of notches (not shown) matching the lugs 344 on the outer cover, so that the indicator wheel can be inserted into the outer cover past the lugs or, alternatively, the elements may configure with some flexibility so that the indicator wheel can snap past the outer cover lugs. In another alternative, the outer cover skirt 342 may be lengthened so that the indicator wheel is positioned above the outer cover lugs and rotatably held in place with an annular bead extending around the inner surface of the skirt. The bead and indicator wheel are sufficiently flexible to allow the indicator wheel to be snapped past the bead. A set of indicator symbols 360 is on the upper surface of the indicator wheel 314 of a size and location such that one indicator symbol at a time is visible through the indicator window 354 in the top portion 340 of the outer cover 312.

The indicator wheel 314 includes at least one pawl 364 located on the outer edge of the indicator wheel to engage the teeth 350 in the outer cover 312. The pawl includes a ramp 366 sloped upward from the flat surface of the indicator wheel, a radially curved outer surface 368 following the circumference of the indicator wheel and a lower surface 370 which is raised relative to the indicator wheel lower surface in order to leave a space under the pawl. The pawl is connected to the indicator wheel at the base of the pawl ramp 366. It is not connected to the indicator wheel at its radially inner side, there being a slot between the pawl inner side and the indicator wheel. The configuration of the pawl and its attachment to the indicator wheel allow the teeth 350 of the outer cover to flex the pawl downward into the space under the pawl as the teeth pass over the pawl.

In operation, the outer cover 312 and indicator wheel 314 are held together by the outer cover lugs 344 or a snap bead as previously described and can be sold and used as a unit. When attaching the unit of the outer cover 312 and indicator wheel 314 to the container 320, the unit is positioned over the container 320 with the outer cover skirt 342 extending over the container upper rim 324. This causes the indicator wheel 314 lower surface to rest on the container upper rim 324. The outer cover 312 is then pressed toward the container 320, thereby compressing the spring 345 in the indicator wheel 314. At the same time, the unit of the outer cover 312 and indicator wheel 314 is rotated (clockwise in the embodiment shown) so that the outer cover lugs 344 ride down the leading edge 328 of the container bayonet lugs 326. As the outer cover lugs 344 pass the rear of the container bayonet lug leading edges 328, the outer cover lugs 344 snap into the container bayonet lug notches 330. The snapped position maintains sufficient pressure between the lower surface of the indicator wheel 314 and container upper rim 324 to seal the container 320. It can be seen that the outer cover positioned as described on the container cannot be removed by merely rotating the outer cover with respect to the container, because the outer cover lugs 344 are held by the container bayonet lugs 326.

To remove the outer cover from the container, it is necessary to push the outer cover toward the container against the force of the indicator wheel spring 345, so that the outer cover lugs 344 move lower than the rear part of the container bayonet lug leading edges 328. Then the outer cover can be rotated in a direction to move the outer cover lugs 344 past the container bayonet lug leading edges 328 and thereby disengage them. It can be appreciated from the drawings that the disengagement procedure will cause the outer cover 312 to rotate relative to the indicator wheel 314 as the friction between the lower surface of the indicator wheel and the upper rim 324 of the container tends to hold the indicator wheel in place. This rotation will cause the outer cover teeth 350 to advance past the indicator wheel ratchet 364, thereby advancing a new one of the indicator symbols 360 under the outer cover window 354. At the same time, the indicator wheel pawl 364 moves over an outer cover tooth 350, and the sudden snapping of the pawl past the tooth results in an audible click which confirms the proper advancement of the indicator wheel. It is important that there be sufficient friction between the indicator wheel and the top of the container so that the indicator wheel is initially held stationary on the container and the outer cover is rotated relative to the indicator wheel to advance the indicator window to a new window. That friction can be obtained by toughening the sliding surfaces if necessary.

In a preferred embodiment, the container bayonet lugs 326 are spaced such that the bayonet lug stop 332 of each bayonet lug 326 serves to stop the outer cover 312 from rotating more than one tooth 350 (which corresponds to one indicator symbol 360) past the indicator wheel ratchet 364. Otherwise, the disengagement process will tend to advance the indicator wheel more than a single indicator symbol, thereby compromising the accurate counting of the device.

Figure 8:
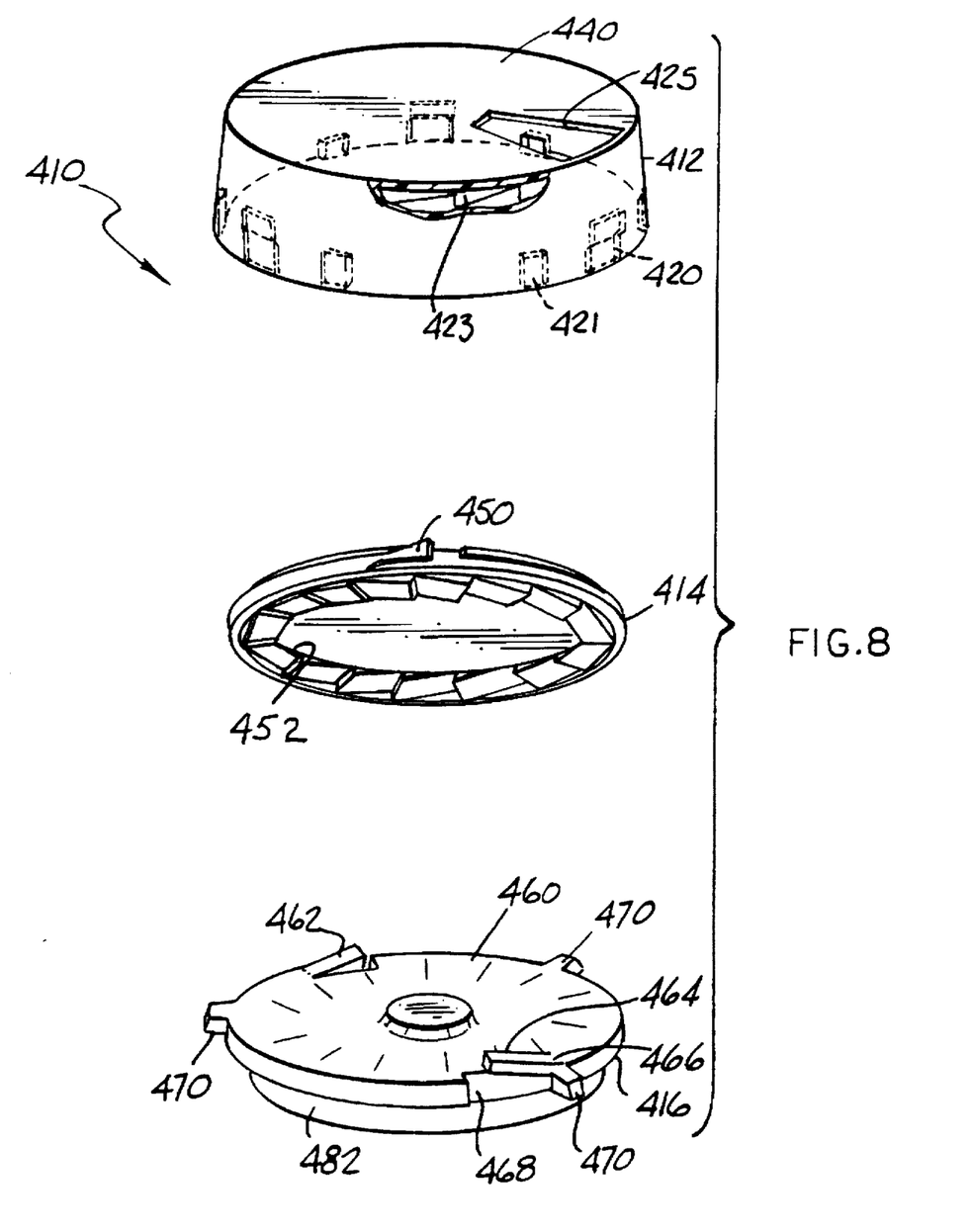
FIG. 8 is an exploded perspective view showing another embodiment of the present invention.

Three-Piece Bayonet Version. Another preferred embodiment is shown in FIG. 8. This embodiment 410 includes an outer cover 412, an indicator wheel 414 and a ratchet wheel 416. The outer cover has the same general outside configuration the outer cover of the previously described two-piece bayonet version. On the inside of the depending skirt are a set of annular grooves 420 with the same configuration as the annular grooves 28 shown in FIG. 1 in connection with the four piece threaded version. The indicator wheel 414 has a pawl 450 and set of teeth 452 in the same manner as the indicator wheel 14 shown in FIG. 1 in connection with the four piece threaded version.

The ratchet wheel 416 is unique to this embodiment. It includes an upper surface 460 having at least one upwardly extending pawl 462 (two in the embodiment shown). Each pawl 462 has an upwardly extending ramp 464 and is flexibly attached to the body of the ratchet wheel 416 at its base 466. The pawl when it flexes downward nests into a cavity 468 in the ratchet wheel body 416. Spaced around the periphery of the upper surface 460 of the ratchet wheel 416 are a set of tabs 470. The tabs 470 are similar to the tabs 270 of the ratchet cover 216 in FIG. 6 shown in connection with the three-piece threaded embodiment 210. They include a radially extending portion, the top surface of which is substantially flush with the top surface of the upper surface 460 and two radially extending substantially parallel sides. The radially outer surface slopes from a smaller radius at the top to a larger radius at the bottom. The number and dimensions of the tabs 470 are such that they can be pressed into the grooves 420 of the outer cover 412 and slide annularly therein.

The bottom surface of the ratchet wheel 416 has a disk 482 coaxially attached thereto. The disk is to mate with and seal against the rim of a container (such as the rim 324 of the container 320 in FIG. 7 shown in connection with the two-piece bayonet version) and may have a beveled resilient circumferential sealing edge.

The upper surface of either the indicator wheel 414 or ratchet wheel 416 may have a convex diaphragm spring in the manner of the embodiments previously described, in order to bias the outer cover 412 away from the container. Also, the pawls and teeth on the ratchet wheel and indicator wheel may be reversed as described for the other embodiments.

In operation, the device 410 is attached to a container (such as the container 320 in FIG. 7 shown in connection with the two-piece bayonet version) by placing it over the container, applying an axial force sufficient to overcome the force of the diaphragm spring and drive the outer cover lugs 421 below the leading edge 328 of the bayonet lugs 326, and then rotating the outer cover 412 in a direction to cause the outer cover lugs 421 to ride past the bayonet lug leading edges 328 and into the bayonet lug notches 330. As this happens, it can be seen that the ratchet wheel 416 remains stationary on the container 320 because the ratchet wheel tabs 470 must move from one end to the other through the outer grooves 420. The indicator wheel 414, however is rotating in unison with the outer cover 412 because the outer cover teeth are engaging the indicator wheel pawl 450. Therefore, the rotating indicator wheel 414 relative to the stationary ratchet wheel 416 causes the ratchet wheel pawls 462 to pass over the indicator wheel teeth 452. As the pawl 462 snaps over a single tooth 452, it makes an audible click to confirm the proper operation of the system. The bayonet lugs 326 on the container 320 are spaced such that the outer cover 412 can be rotated only enough for the ratchet wheel pawls 462 to pass over a single indicator wheel tooth 452 before the outer cover lugs 421 are stopped by the stop 332 of the bayonet lug 326. It can be appreciated that there must be enough friction between the container and the ratchet wheel to hold the ratchet wheel and indicator wheel stationary in the container as the outer cover is initially rotated, so that the indicator window advances to a new indicator symbol.

To remove the device 410 from the container 320, an axial force is applied to move the outer cover lugs 421 below the bayonet lug leading edges 328, and then the outer cover is rotated in a direction opposite the direction of rotation to attach the device to the container. Initially, the friction of the ratchet wheel 416 against the container rim 324 causes the ratchet wheel to remain stationary. The stationary ratchet wheel 316 holds the indicator wheel 414 stationary by the engagement of the ratchet wheel pawls 462 in the indicator wheel teeth 452. The stationary indicator wheel 414 relative to the rotating outer cover 412 causes the indicator wheel pawl 450 to pass over the outer cover teeth 423. The snapping of the indicator wheel pawl 450 over a single outer cover tooth 423 causes an audible click to confirm the proper operation of the device.

As the outer cover 412 rotates relative to the indicator wheel 414, the outer cover indicator symbol window 425 advances to a new indicator symbol. The bayonet lugs 326 and outer cover lugs 421 are numbered and spaced such that the outer cover can rotate through the angle necessary for the ratchet wheel tabs to move through the outer cover grooves, (corresponding to a single tooth and single indicator symbol) before the outer cover lug 421 is stopped by the back of the bayonet lug 326 adjoining the bayonet lug 326 from which the outer cover lug 421 was just removed.

It can be appreciated that the three-piece bayonet embodiment described above is configured such that an audible click results as the device is securely attached to the container. Another audible click results as the device is removed from the container and the indicator window advances to the next indicator symbol.

Figure 9:
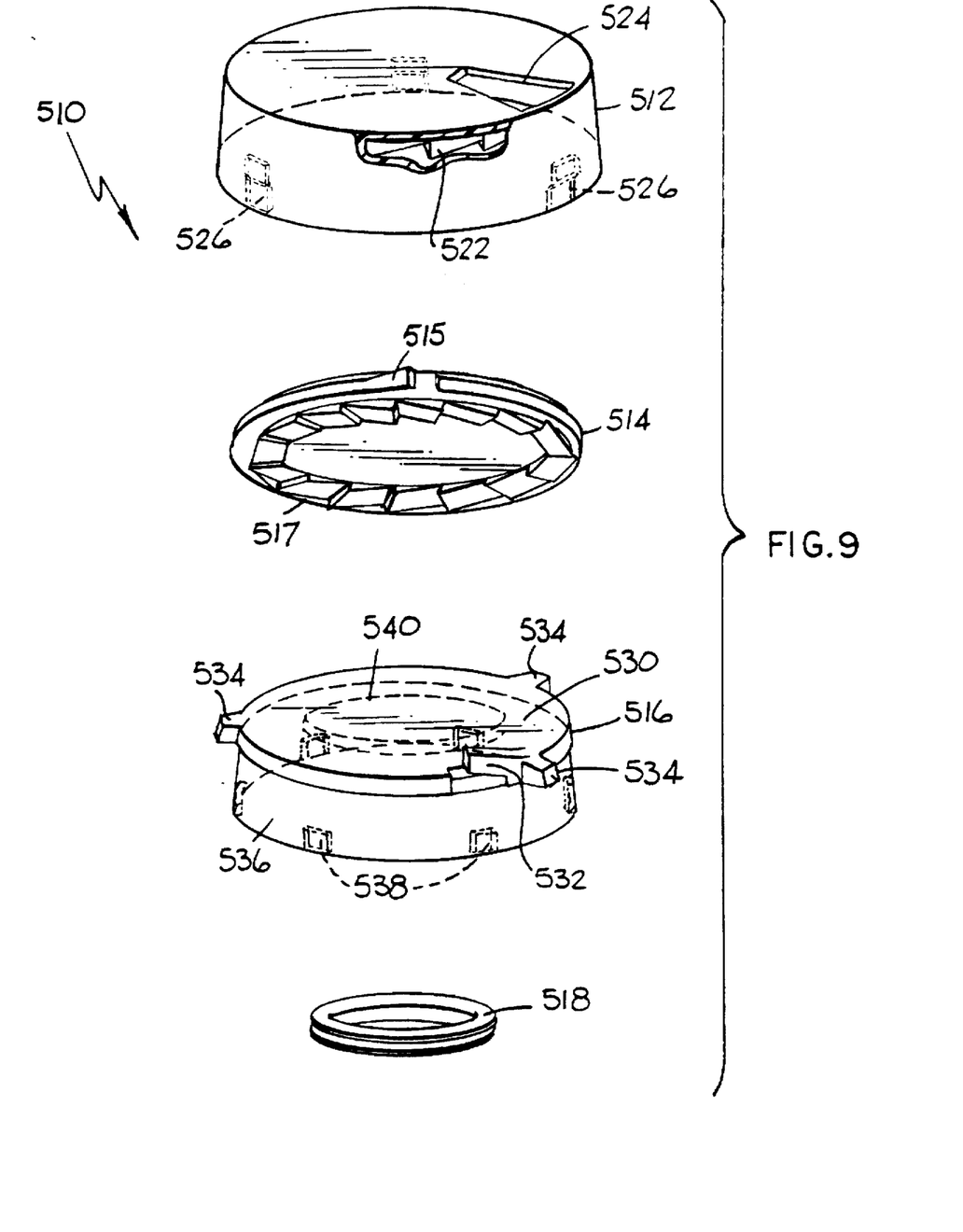
FIG. 9 is an exploded perspective view showing another embodiment of the present invention.
Figure 10:
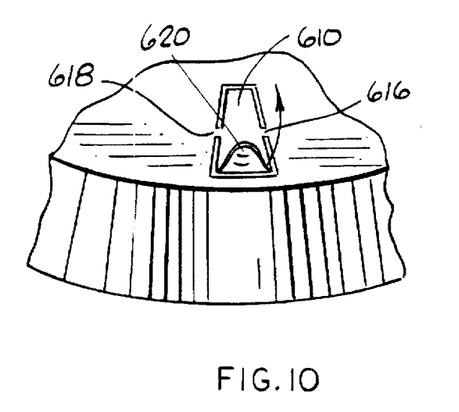
FIG. 10 is a partial perspective view of a detail of the present invention.

Alternate Three-Piece Bayonet Version. Another preferred embodiment 510 is shown in FIG. 9 for use with a bayonet lug container such as the container 320 in FIG. 7 shown in connection with the two-piece bayonet version. The main elements are an outer cover 512, an indicator wheel 514, a ratchet cover 516, and a seal 518 which may or may not be integral with the ratchet cover 516. The outer cover 512 includes a set of outer cover teeth 522, an indicator symbol window 524 and a set of annular grooves 526, all of which are essentially the same as those shown in FIG. 8 in connection with the three-piece bayonet version. However, this embodiment differs from the embodiment shown in FIG. 8 in that this embodiment has no lugs on the outer cover. The indicator wheel 514 is essentially the same as the indicator wheel 414 shown in FIG. 8.

The ratchet cover of this embodiment includes an upper portion 530 with at least one ratchet cover pawl 532 and a set of spaced tabs 534 to engage and slide in the annular grooves 526 of the outer cover 512, again all essentially the same as the corresponding elements shown in FIG. 8. The ratchet cover 516 also has an axially depending skirt 536 which is attached to or integral with the top portion 530. The skirt 536 has a set of lugs 538 spaced around its inner surface which are numbered and dimensioned to engage the bayonet lugs 326 of the container 320. The lower surface of the top portion 530 has an annularly extending ring 540 to receive the seal 518. The seal 518 is an ordinary resilient disk that attaches to the ring 540 of the ratchet cover and seals the container 320 upon engagement of the device 510 with the container.

In operation, the device 510 is placed over the container 320, an axial force is applied to overcome the resistive axial force applied by the compression of the seal 518, and the outer cover 512 is rotated in a direction to urge the ratchet wheel lug 538 into engagement with the bayonet lugs 326 of the container 320. Initially, the ratchet wheel 516 and ratchet wheel lugs 538 remain stationary as the ratchet wheel tabs 534 slide through the outer cover grooves 526. During this time, the engagement of the outer cover teeth 522 with the indicator wheel pawl 515 causes the indicator wheel 514 to rotate with the outer cover 512. This rotation by the indicator wheel 514 relative to the ratchet cover 516 causes the ratchet cover pawl 532 to pass over a tooth of the indicator wheel teeth 517, thereby producing an audible click.

When the ratchet cover tabs 534 reach the end of the outer cover grooves 526, then the ratchet cover 516 is forced to rotate with the outer cover 512. This ratchet cover rotation causes the ratchet cover lugs 538 to engage the container bayonet lugs 326 so that the lugs become positioned in the bayonet lug notches 330 where rotation is stopped by the bayonet lug stops 332.

To remove the device 510 from the container 320, an axial force is again applied to overcome the resistive sealing force of the seal 518, and the outer cover is rotated in the direction opposite the direction for attachment of the device. Initially, the ratchet cover 516 remains stationary as the ratchet cover tabs 534 slide to the other end of the outer cover grooves 526. As that occurs, the engagement of the ratchet cover pawl 532 with the indicator wheel teeth 517 keep the indicator wheel 514 stationary with the ratchet cover 516. This causes a rotation of the outer cover 512 relative to the indicator wheel 514, thereby passing the indicator wheel pawl 515 over an outer cover tooth 522 to cause an audible click and advancing the indicator symbol window 524 to a new indicator symbol. After the ratchet wheel tabs 534 reach the end of the outer cover grooves 526, the ratchet cover 518 is forced to rotate with the outer cover 512, thereby causing the ratchet cover lugs 538 to move past the leading edge 328 of the bayonet lugs 326 so that the device 510 can be removed from the container 320.

It can be seen that this embodiment has the advantage that all the "lost motion" that causes the audible clicks to confirm proper operation and the advancement of the indicator window is dependent solely on the motion of the ratchet wheel tabs through the outer cover grooves, and is not related to the spacing of the bayonet lugs. Therefore, this embodiment has the advantage that it can be used with a standard bayonet lug spacing that has no relation to the number of teeth in the outer cover or indicator wheel or the number of indicator symbols.

FIGS. 10–13 show an arrangement for blocking the window 22 shown in connection with the embodiment in FIG. 1 or any of the other embodiments herein. The purpose of such an arrangement is to allow the user of the device to choose whether or not to use the counting feature of the device. In the embodiment shown in FIG. 10, the block employs a window cover 610 that is attached to the border of the window 22 with two snap tabs 616 and 618. The radially outer edge of the cover 610 has an axially extending tab 620. In operation, the user grasps the tab 620 and breaks the cover 610 free of the window 22 by snapping the snap tabs 616 and 618, thereby exposing the window 22.

Figure 11:
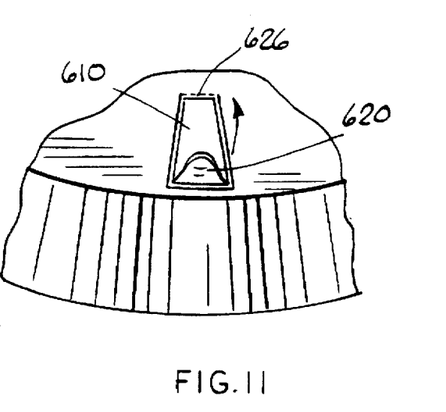
FIG. 11 is a partial perspective view of a detail of an alternative embodiment of the present invention.
Figure 12:
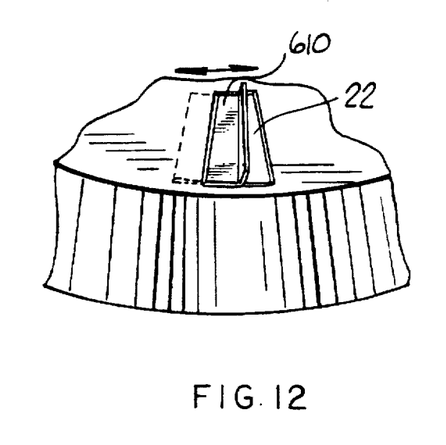
FIG. 12 is a partial perspective view of a detail of an alternative embodiment of the present invention.
Figure 13:
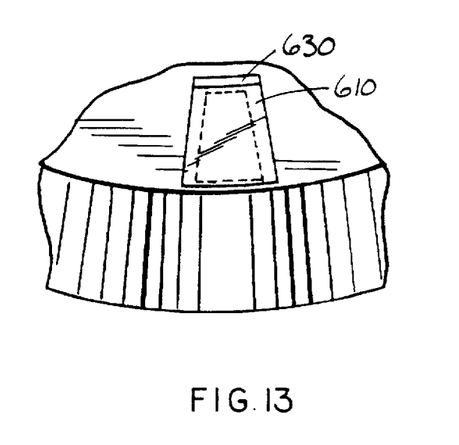
FIG. 13 is a partial perspective view of a detail of an alternative embodiment of the present invention.
Figure 14:
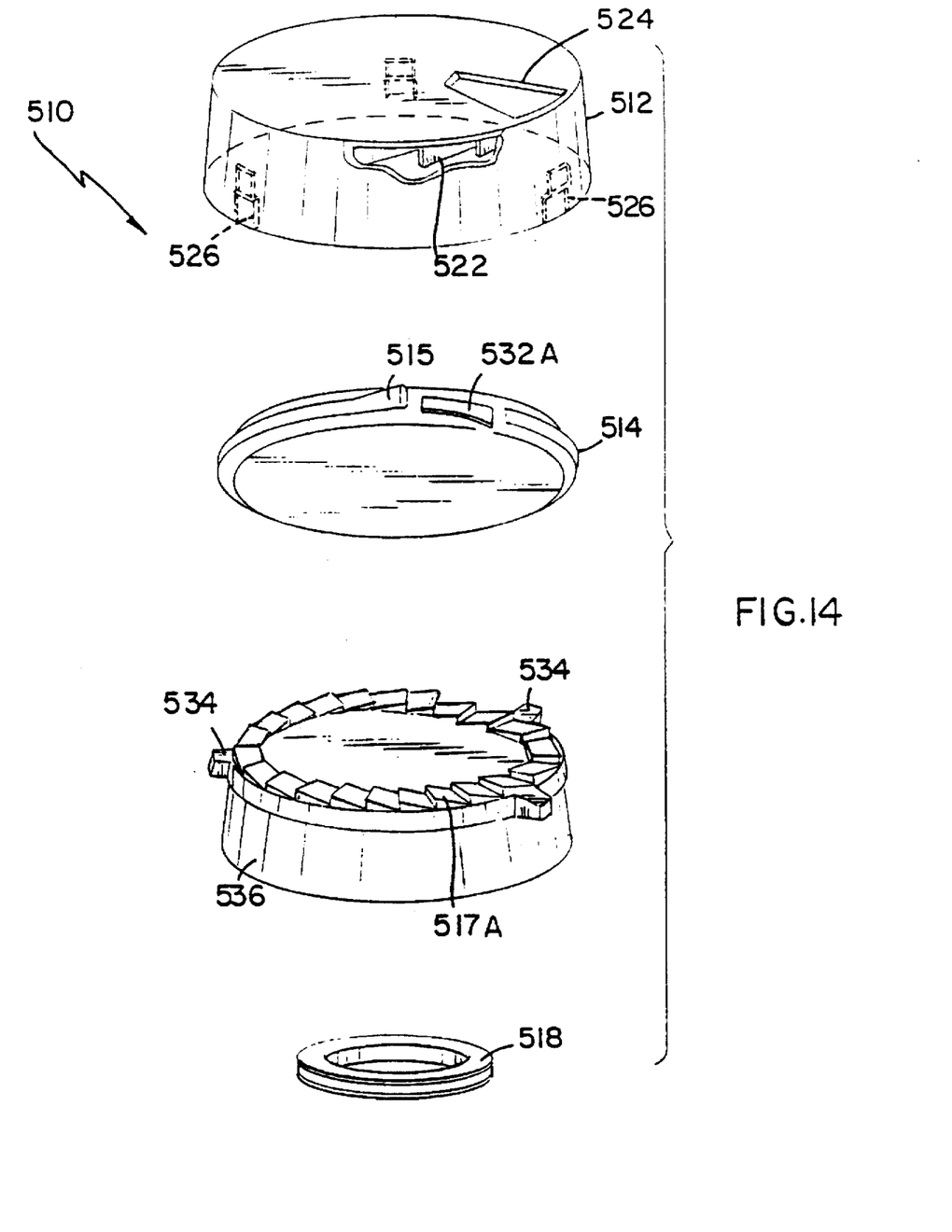
FIG. 14 is an exploded perspective view showing another embodiment of the present invention.

FIGS. 11–13 show several variations on the window cover. In FIG. 11, the snap tabs of FIG. 10 are replaced with a flexible hinge 626 at the radially inner edge of the cover 610. Depending on the design considerations, the hinge may be constructed to keep the cover attached to the device by flexing upward, or may be constructed to break so that the cover separates from the device. In FIG. 12, the cover 610 slides into the outer cover 12 to reveal the window 22. In FIG. 13, the cover 610 is a removable adhesive tape with a nonadhesive portion 630 at one side for the user to grasp to remove the tape to expose the window.

What is claimed is:

1. An indicator closure for closing a contains, comprising: an outer cover and an indicator mechanism disposed between the outer cover and the container whereby the indicator mechanism is rotatable in relation to the outer cover to indicate the attachment or removal of the indicator closure in relation to the container; a first set of teeth and a first pawl engaged between the outer cover and indicator mechanism to allow rotation of the outer cover relative to tho indicator mechanism in a first direction but not in a second direction opposite the first direction, said first pawl extending radially and circumferentially from the indicator mechanism, said first pawl free of locking engagement with said retainer at all times; a retainer disposed between the indicator mechanism and the container; a set of annular stops and at least one tab received between the stops engaged between the outer cover and retainer, the at least one tab extending in a radial direction from the retainer, whereby the rotation of the retainer in relation to the outer cover is limited by the tab abutting against the stops; and a second set of teeth and a second pawl engaged between the indicator mechanism and retainer to allow rotation of the indicator mechanism relative to the retainer in said second direction but not in said first direction.

2. The indicator closure of claim 1, further comprising an axially depending skirt on the outer cover, the axially depending skirt having a set of bayonets adapted to engage a set of bayonet lugs on the container.

3. The indicator closure of claim 2, wherein the set of bayonets and bayonet lugs are spaced such that the indicator wheel advances by a single indicator symbol upon rotating said outer cover an amount sufficient to remove said closure from said container.

4. The indicator closure of claim 1, further comprising an axially depending skirt on the outer cover, the axially depending skirt having a set of bayonet lugs adapted to engage a set of bayonets on the container.

5. The indicator closure of claim 4, wherein the set of bayonets and bayonet lugs are spaced such that the indicator wheel advances by a single indicator symbol upon rotating said outer cover an amount sufficient to remove said closure from said container.

* * * * *